United States Patent
Colley et al.

(10) Patent No.: US 6,809,217 B1
(45) Date of Patent: *Oct. 26, 2004

(54) PROCESS FOR THE PREPARATION OF ETHYL ACETATE

(75) Inventors: Stephen William Colley, Dormanstown (GB); Christopher Richard Fawcett, London (GB); Colin Rathmell, Yarm (GB); Michael William Marshall Tuck, London (GB)

(73) Assignee: Davy Process Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/806,184

(22) PCT Filed: Sep. 29, 1999

(86) PCT No.: PCT/GB99/03230

§ 371 (c)(1),
(2), (4) Date: Jun. 5, 2001

(87) PCT Pub. No.: WO00/20375

PCT Pub. Date: Apr. 13, 2000

(30) Foreign Application Priority Data

Oct. 1, 1998 (EP) .......................... 98308011

(51) Int. Cl.[7] .......................... C07C 69/02; C07C 67/00
(52) U.S. Cl. .................. 560/231; 560/238; 560/239
(58) Field of Search ................. 560/231, 233, 560/239, 238, 265

(56) References Cited

U.S. PATENT DOCUMENTS 1,708,460 A * 4/1929 Zeisberg
2,027,182 A * 1/1936 Lazier ........................ 260/156
2,524,899 A   10/1950 Dunn (List continued on next page.)

FOREIGN PATENT DOCUMENTS

| EP | 0 101 910 A1 | 3/1984 |
| EP | 0 151 886 A1 | 8/1985 |
| EP | 0 201 105 A1 | 11/1986 |

(List continued on next page.)

OTHER PUBLICATIONS

"Selective Reduction of Acetic Acid to Acetaldehyde on Iron Oxides" Grootendorst et al. J. Catalysis. vol. 148, pp261–269 (1994).*
James R. Fair, "Distillation" excerpt from Kirk–Othmer Encyclopedia of Chemical Technology (1993).*
International Search Report for International Application No. PCT/GB 99/03230, mailed Jan. 19, 2000.
Abstract of Brazilian Application No. PI 9104652A, dated Apr. 27, 1993.

(List continued on next page.)

*Primary Examiner*—Richard L. Raymond
*Assistant Examiner*—Zachary C. Tucker
(74) *Attorney, Agent, or Firm*—Senniger Powers

(57) ABSTRACT

Ethanol is dehydrogenated in the presence of hydrogen over a dehydrogenation catalyst, for example, a copper on silica catalyst. The liquefiable products present in the resulting intermediate reaction product mixture are selectively hydrogenated over a suitable catalyst, such as 5% ruthenium on carbon, so as selectively to hydrogenate reactive carbonyl-containing by-products to the corresponding alcohols. Butan-2-one and n-butyraldehyde are thereby hydrogenated to 2-butanol and n-butanol respectively. A two stage distillation procedure is then used to purify the selectively hydrogenated product. A first distillate of ethyl acetate, ethanol and water produced in the first distillation zone is redistilled in the second distillation zone, thereby producing a bottom product comprising, typically, from about 99.8 mol % to about 99.95 mol % ethyl acetate and an overhead second distillate, which has a different composition from that produced in the first distillation zone and which is returned to the first distillation zone.

29 Claims, 3 Drawing Sheets

U.S. PATENT DOCUMENTS

| | | | |
|---|---|---|---|
| 3,714,236 | A | 1/1973 | Wright, Jr. et al. |
| 4,052,424 | A | 10/1977 | Vanderspurt |
| 4,220,803 | A | 9/1980 | Marcinkowsky et al. |
| 4,379,028 | A | 4/1983 | Berg et al. |
| 4,395,576 | A | 7/1983 | Kwantes et al. |
| 4,440,946 | A | 4/1984 | Summerville et al. |
| 4,481,146 | A | 11/1984 | Leupold et al. |
| 4,523,027 | A | 6/1985 | Kummer et al. |
| 4,569,726 | A | 2/1986 | Berg et al. |
| 4,613,701 | A | 9/1986 | Strong |
| 4,946,029 | A | 8/1990 | Frank et al. |
| 5,334,751 | A | 8/1994 | Lemanski et al. |
| 6,632,330 | B1 | 10/2003 | Colley et al. |

FOREIGN PATENT DOCUMENTS

| | | |
|---|---|---|
| EP | 0 331 021 A1 | 9/1989 |
| GB | 287846 | 4/1929 |
| GB | 312345 | 8/1930 |
| GB | 470773 | 8/1937 |
| JP | 59-25334 | 2/1984 |
| JP | 5-186392 | 7/1993 |
| SU | 362814 | 11/1973 |
| WO | WO 00/20373 A1 | 4/2000 |

OTHER PUBLICATIONS

Shigeaki Nakumura and Kazuaki Kawamoto, *The Catalytic Dehydrogenation of Alcohols with Reduced Copper under Ultraviolet Light,* Bulletin of the Chemical Society of Japan, 1971, vol. 44, No. 4, pp. 1072–1078.

Kenji Takeshita, Shigeaki Nakamura, and Kazuaki Kawamoto, *Reduced Copper Catalyzed Conversion of Primary Alcohols into Esters and Ketones,* Bulletin of the Chemical Society of Japan, 1978, vol. 51, No. 9, pp. 2622–2627.

Abstract of Japanese Patent Application No. 59025334.

Abstract of Japanese Patent Application No. 5186392.

U.S. patent application Ser. No. 09/806,180, Colley et al., filed Jun. 5, 2001.

Breitner, Edith, et al., *Low Pressure Hydrogenation of Ketones with Platinum Metal Catalysts,* Hydrogenation Carbonyl Compounds Over Platinum Metal Catalysts, [reprinted from the Journal of Organic Chemistry, 24, 1855 (1959)], pp. 1–3.

Engelhard Catalysts, Summary, 1977, 3 pages.

Heterogeneous Catalysis, Products and Services, Johnson Matthey Chemicals, Limited, 1981–1984, 6 pages.

Matar, Sami, et al., Catalysis in Petrochemical Processes, 1989, p. 260, Kluwer Academic Publishers.

Rylander, Paul N., Catalytic Hydrogenation over Platinum Metals, 1967, p. 245, Academic Press, New York and London.

Stiles, Alvin B., Catalyst Supports and Supported Catalysts, 1987, p. 132, Butterworth Publishers, Stoneham, MA.

* cited by examiner

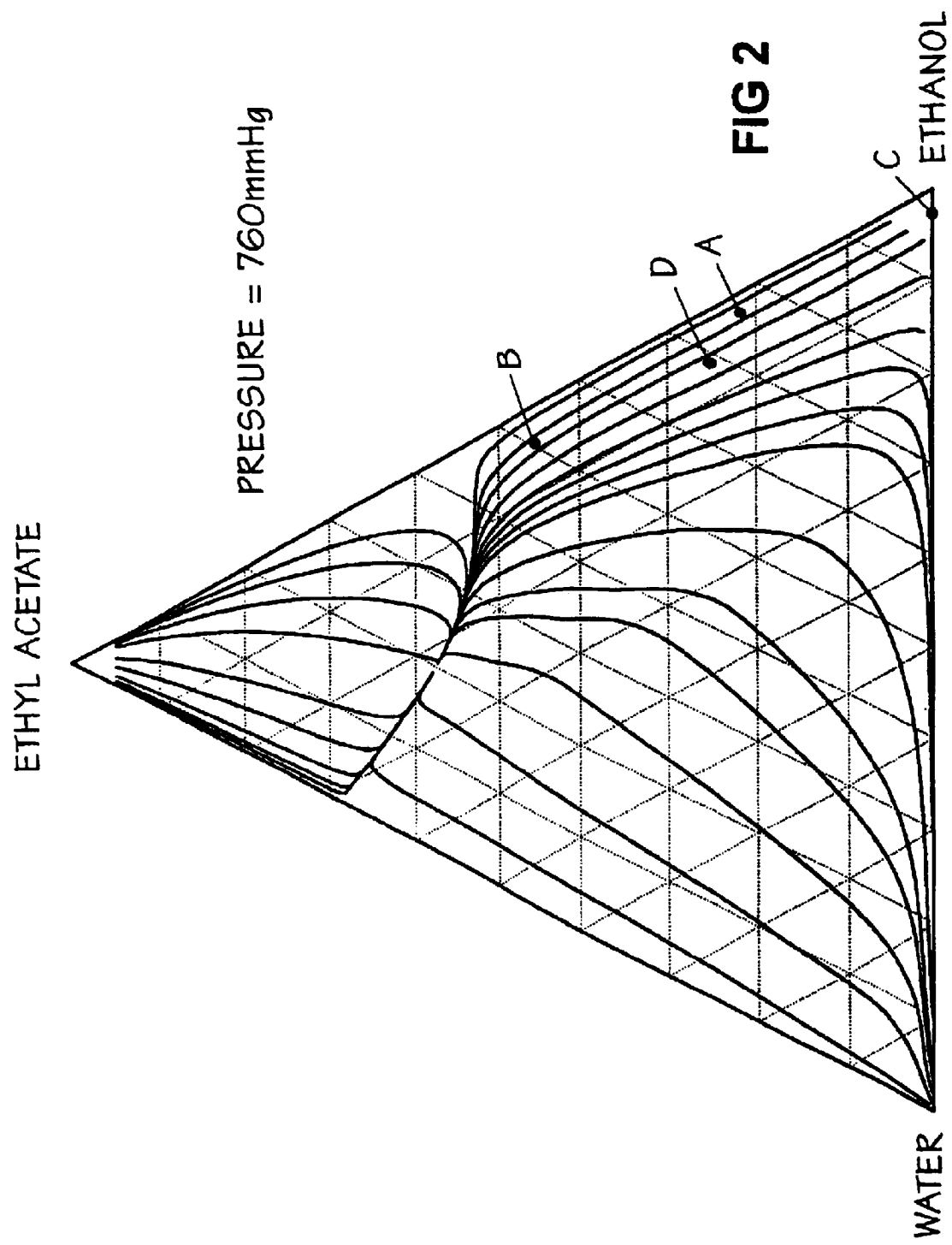

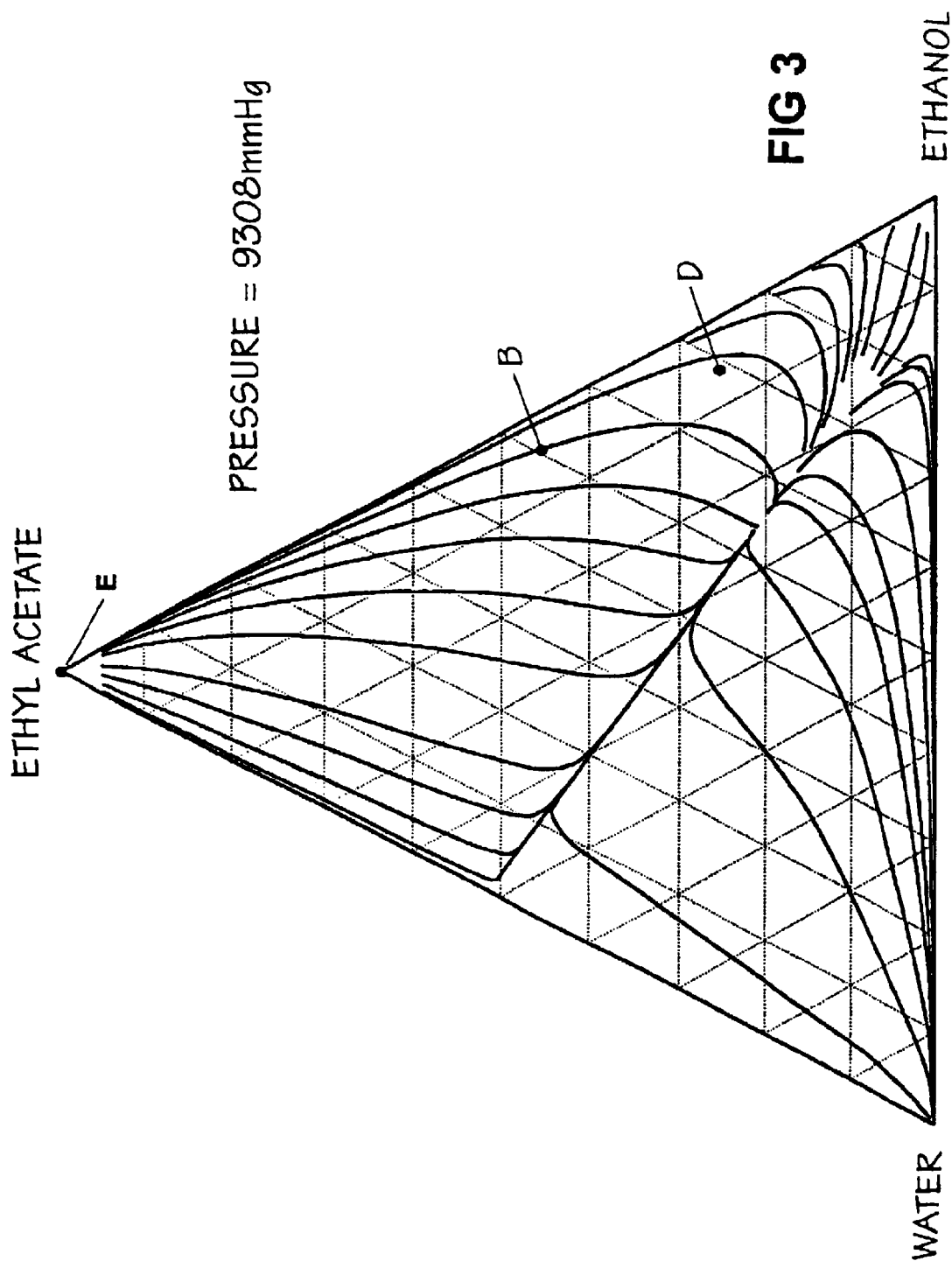

PROCESS FOR THE PREPARATION OF ETHYL ACETATE

This application was filed under 35 U.S.C. 371, and is the U.S. National Stage of PCT/GB99/03230, filed Sep. 29, 1999.

This invention relates to a process for the production of ethyl acetate.

Etyl acetate is a relatively expensive bulk chemical which is conventionally produced by esterification of acetic acid with ethanol according to equation (1):

$$CH_3.CO.OH+CH_3CH_2OH=CH_3.CO.O.CH_2.CH_3+H_2O \qquad (1).$$

Because this reaction does not tend to lead to formation of by-products which have boiling points close to that of ethyl acetate, recovery of substantially pure ethyl acetate from the esterification product mixture is usually not complicated by the presence of by-products of the esterification reaction.

Some other methods which have been proposed for the conversion of ethanol to ethyl acetate, however, tend to lead to formation of by-products, notably n-butyraldehyde and butan-2-one, which have boiling points close to that of ethyl acetate and hence make the recovery of substantially pure ethyl acetate from the resulting reaction product mixtures more difficult than from esterification reaction mixtures. These methods include dehydrogenation of ethanol, oxidation of ethanol, reaction of ethanol with acetaldehyde, and oxidation of ethanol to acetaldehyde followed by the Tischenko reaction.

Ethyl acetate can be produced from acetaldehyde according to the Tischenko reaction given in equation (2):

$$2CH_3.CHO=CH_3.CO.O.CH_2.CH_3 \qquad (2).$$

It is also possible to produce ethyl acetate from ethanol by dehydrogenation according to equation (3):

$$2CH_3.CH_2.OH=CH_3.CO.O.CH_2.CH_3+2H_2 \qquad (3).$$

According to China Chemical Reporter, 26 Mar. 1996, a plant with a capacity of 5000 tonnes per annum for production of ethyl acetate by dehydrogenation of ethanol has been constructed at Linshu Chemical Fertilizer Plant of Shandong using a catalyst developed by Qinghua University.

Ethanol is produced in large quantity by a variety of processes, including hydration of ethylene, the Fischer Tropsch process, or as a fermentation product. The purity of the ethanol often depends upon the method used for its production. For example, although hydration of ethylene yields a substantially pure ethanol product, the Fischer Tropsch process yields also a number of by-products which are troublesome to remove from the ethanol product. In the case of fermentation, the ethanol product is obtained as an aqueous solution which may also contain by-products whose removal from the ethanol is difficult.

In certain circumstances ethanol may be available in excess capacity, whilst acetic acid is not readily available in the necessary quantity. Accordingly, there are many reasons why, particularly in countries having a relative abundance of ethanol with respect to acetic acid, it is commercially interesting to produce ethyl acetate from ethanol, acetaldehyde or a mixture thereof.

Catalytic dehydrogenation of alcohols with reduced copper under ultra violet light was described by S. Nakamura et al, in *Bulletin of the Chemical Society of Japan* (1971), Vol. 44, pages 1072 to 1078.

K. Takeshita et al described reduced copper catalysed conversion of primary alcohols into esters and ketones in *Bulletin of the Chemical Society of Japan*, (1978) Vol. 51(9), pages 2622 to 2627. These authors mention that the mechanism for ester formation has been described in the literature as the Tischenko reaction. That is to say that dehydrogenation of ethanol yields acetaldehyde as an intermediate which combines according to the Tischenko reaction to produce ethyl acetate. Alternatively, or as well, 1 mole of ethanol may combine with 1 mole of acetaldehyde to yield 1 mole of ethyl acetate and 1 mole of hydrogen according to equation (4)

$$CH_3CH_2OH+CH_3.CHO=CH_3.CO.O.C_2.CH_3+H_2 \qquad (4).$$

U.S. Pat. No. 4,996,007 teaches a process for the oxidation of primary alcohols to aldehydes, acids and esters, particularly to aldehydes. In this process a primary alcohol is contacted, together with molecular oxygen, with a catalyst selected from ruthenium, rhodium, platinum, palladium, rhenium and mixtures thereof, optionally a quaternary $C_1$ to $C_{20}$ alkyl ammonium cocatalyst, and as oxygen activator dihydrodihydroxynaphthalene, dihydrodihydroxyanthracene or a mixture thereof. The product aldehydes, acids and esters are then separated from the reaction mixture.

In U.S. Pat. No. 4,220,803 catalytic dehydrogenation of ethanol for the production of acetaldehyde and acetic acid using a supported copper oxide essentially free of barium is proposed.

A silver-cadmium alloy catalyst has been suggested for use in production of alkyl alkanoate esters, by contacting a primary alkanol in the vapour phase with the catalyst at a temperature of between about 250° C. and 600° C., in U.S. Pat. No. 4,054,2424.

In U.S. Pat. No. 4,440,946 there is described a process for producing a carboxylate ester which comprises contacting a mixture of alcohol and aldehyde in the vapour phase with a coprecipitate composition comprising silver-cadmium-zinc-zirconium which is substantially in the free metal form.

Use of the Tischenko reaction for the production of mixed esters from aldehydes is described in U.S. Pat. No. 3,714,236.

U.S. Pat. No. 5,334,751 teaches production of ethyl acetate by reaction of ethanol and oxygen in the presence of a solid catalyst that contains crystalline $TiP_2O_7$ and has the formula $Pd_aM_bTiP_cO_7$, where M is Cd, Au, Zn, Tl, or an alkali metal or alkaline earth metal, a is 0.0005–0.2, b is 0.3a, c is 0.5–2.5, x has a value to satisfy the valencies, and Ti and P of the crystalline $TiP_2O_7$ represent part of the crystalline $TiP_2O_7$.

BR-A-91/04652 teaches pre-treatment of a palladium on a silica carrier catalyst for production of ethyl acetate by direct oxidation of ethanol with air.

Production of esters from primary alcohols by dehydrogenation using bromous acid or a salt thereof in acid medium is described in JP-A-59/025334.

In SU-A-362814 there is described a process for production of ethyl acetate by dehydrogenation of ethanol at 180° C. to 300° C. in the presence of a copper catalyst containing zinc as an activator with an ethanol feed rate of 250 to 700 liters per liter of catalyst per hour.

The dehydrogenation of ethanol to form ethyl acetate is described in GB-A-287846. This proposes use of a dehydrogenating agent, such as a copper catalyst, a temperature of from 250° C. to 500° C., and a pressure of more than 10 atmospheres ($1.013 \times 10^6$ Pa).

Vapour phase contact of ethanol at a temperature above its critical temperature with a catalyst comprising copper and a difficultly reducible oxide, such as zinc oxide or manganese oxide, is proposed in GB-A-312345, use of a temperature of 375° C. and a pressure of 4000 psi (27.58 Mpa) being suggested.

GB-A-470773 teaches a process for conversion of ethanol to ethyl acetate by dehydrogenating ethanol over a catalyst consisting of a reduced metal, for example, copper on infusorial earth with 10% uranium oxide as promoter, maintained at a temperature of 220° C. to 260° C., removing by condensation some of the gas-vapour product rich in hydrogen resulting from the reaction, and returning the gaseous remainder rich in hydrogen to the catalysing zone.

EP-A-0151886 describes a process for the preparation of $C_{2+}$ esters of alkyl carboxylic acids from $C_{2+}$ primary alcohols which comprises contacting a vaporous mixture containing a primary $C_{2+}$ alkanol and hydrogen in an alkanol:hydrogen molar ratio of from 1:10 to about 1000:1 at a combined partial pressure of alkanol and hydrogen of from about 0.1 bar ($10^3$ Pa) up to about 40 bar ($4 \times 10^6$ Pa) and at a temperature in the range of from about 180° C. to about 300° C. in a catalytic reaction zone with a catalyst consisting essentially of a reduced mixture of copper oxide and zinc oxide, and recovering a reaction product mixture containing a primary $C_{2+}$ alkyl ester of an alkyl carboxylic acid which ester contains twice as many carbon atoms as the primary $C_{2+}$ alkanol.

In EP-A-0201105 there is described a method for converting primary alcohols, such as ethanol, to their corresponding alkanoate esters which involves the regulation of the mole feed ratio of hydrogen gas to alkanol in the reaction zone of a copper chromite containing catalyst.

One method of separating ethyl acetate from ethanol and water involves extractive distillation with an extractive agent comprising polyethylene glycol and dipropylene glycol, diethylene glycol, or triethylene glycol as described in U.S. Pat. No. 4,569,726 or with an extractive agent containing dimethyl sulphoxide as described in U.S. Pat. No. 4,379,028.

Separation of ethyl acetate from a composition comprising ethyl acetate, ethanol and water is disclosed in JP-A-05/186392 by feeding the composition to a distillation column to obtain a quasi-azeotropic mixture comprising ethyl acetate, ethanol and water, condensing it, separating the condensate into an organic layer and an aqueous layer, returning the organic layer to the column, and recovering ethyl acetate as a bottom product from the column.

EP-A-0331021 describes how carbonylation of olefins to produce monocarboxylate esters causes formation of aldehydes and acetals as byproducts. Monocarboxylate esters produced in this way are subjected to a three step purification process involving treatment with a strongly acidic agent, followed by hydrogenation and distillation. The initial treatment with a strongly acidic agent is intended to convert acetals to vinyl ethers and aldehydes and acetals to aldols. The subsequent hydrogenation step then converts these compounds to byproducts which are more easily separated from the desired monocarboxylate ester.

EP-A-0101910 contains a similar disclosure regarding carbonylation of olefins to give monocarboxylate esters. It proposes treatment of the monocarboxylate ester with hydrogen at elevated temperature in the presence of an acidic ion exchanger or zeolite doped with one or more metals of Group VIII of the Periodic Table, followed by hydrogenation. It is stated that acetals present as byproducts are converted to vinyl ethers which are converted by hydrogenation to low boiling esters or the aldehydes and acetals are converted to high boilers by an aldol reaction. Unsaturated ketones are converted to saturated ketones.

It would be desirable to provide an improved commercial method of upgrading ethanol to ethyl acetate, a more valuable product, particularly where there is an over-capacity for ethanol. It would also be desirable to provide a novel route to high purity ethyl acetate which obviates the need for a separate acetaldehyde or acetic acid plant. It would further be desirable to provide a process for the production of substantially pure ethyl acetate directly from ethanol without the need to convert part of the ethanol feedstock to acetaldehyde or to acetic acid. Additionally it would be desirable to provide a route to ethyl acetate by dehydrogenation of ethanol which is capable to yielding high purity ethyl acetate from ethanol feed streams containing significant amounts of impurities.

One particular problem in production of ethyl acetate by dehydrogenation of ethanol is that the reaction product mixture tends to be a complex mixture including esters, alcohols, aldehydes and ketones. The reaction mixture can be even more complex when the ethanol feed contains impurities. The reaction product mixtures contain components with boiling points close to ethyl acetate (such as U-butyraldehyde and butan-2-one), including components which can form azeotropes with ethyl acetate, and/or other components of the mixture. This is a particular problem when high purity ethyl acetate is desired. Another problem is that water present in the feed ethanol or produced as a by-product during dehydrogenation has a deactivating effect on dehydrogenation catalysts so that any recycle to the dehydrogenation reactor of unconverted ethanol should desirably contain only a low level, if any, of water.

The present invention accordingly seeks to provide a novel process for production of ethyl acetate from ethanol, enabling production of ethyl acetate at a relatively low cost and involving simple plant. Another object of the present invention is to provide an improved process for the production of high purity ethyl acetate from ethanol, or from a feedstock comprising a major proportion of ethanol and a minor proportion of impurities such as iso-propanol.

According to the present invention there is provided a process for the production of ethyl acetate which comprises:
(a) converting a $C_2$ feedstock comprising ethanol to ethyl acetate in an ethyl acetate production zone by a procedure selected from:
  (i) dehydrogenation,
  (ii) oxidation,
  (iii) reaction with acetaldehyde, and
  (iv) oxidation to acetaldehyde followed by the Tischenko reaction;
(b) recovering from the ethyl acetate production zone an intermediate reaction product mixture comprising hydrogen and liquefiable products comprising ethyl acetate, ethanol, and by-products containing reactive carbonyl groups;
(c) contacting at least a portion of the liquefiable products of the intermediate reaction product mixture with a selective hydrogenation catalyst in the presence of hydrogen in a selective hydrogenation zone maintained under selective hydrogenation conditions effective for selective hydrogenation of by-products containing reactive carbonyl groups thereby to hydrogenate said by-products selectively to hydrogenated by-products comprising corresponding alcohols;
(d) recovering from the selective hydrogenation zone a selectively hydrogenated reaction product mixture comprising ethyl acetate, ethanol, hydrogen and hydrogenated by-products;
(e) distilling material of the selectively hydrogenated reaction product mixture in one or more distillation zones so as to produce a first composition comprising substantially pure ethyl acetate and a second composition comprising ethanol and water;

(f) treating the second composition of step (e) to separate water therefrom and yield a third composition comprising ethanol with a reduced water content; and (g) recovering the third composition of step (f).

In step (a) of the process of the invention the $C_2$ feedstock is converted to ethyl acetate by (i) dehydrogenation, (ii) oxidation, (iii) reaction with acetaldehyde, or (iv) oxidation to acetaldehyde followed by the Tischenko reaction. In all of these processes by-products of the reaction include $C_4$ compounds having boiling points which are close to that of ethyl acetate (b.p. 77.1° C.) and hence give rise to problems in purification of the ethyl acetate product. Notable amongst these by-products are butane-2-one (b.p. 79.6° C.) and n-butyraldehyde (b.p. 75.7° C.). Such by-products are not produced in the course of production of ethyl acetate by esterification of ethanol with acetic acid.

The $C_2$ feedstock used instep (a) comprises ethanol which has been produced by hydration of ethylene, by the Fischer Tropsch process, or by fermentation of a carbohydrate source, such as starch. It may alternatively be a byproduct of another industrial process. It may contain, besides ethanol, minor amounts of water as well as small amounts of impurities resulting from byproduct formation during its synthesis. If the $C_2$ feedstock includes recycled unreacted ethanol, then any by-products formed in the dehydrogenation step which are contained in the recycled ethanol will also contribute to the level of by-products present in the $C_2$ feedstock. Impurities present in the $C_2$ feedstock may include, for example, higher alcohols such as n-propanol, iso-propanol, n-butanol and sec-pentanol; ethers, such as diethyl ether, and di-iso-propyl ether; esters, such as iso-propyl acetate, s-butyl acetate and ethyl butyrate; and ketones, such as acetone, butan-2-one, and 2-pentanone. At least some of these impurities can be difficult to remove from ethyl acetate, even when they are present in quantities as low as about 0.1 mol % or less, by traditional distillation procedures because they have boiling points which are close to that of ethyl acetate and/or form constant boiling mixtures therewith.

In step (a) the $C_2$ feedstock may be subjected to dehydrogenation according to equation (3) above. In this case the $C_2$ feedstock can be converted to ethyl acetate by a dehydrogenation procedure which comprises contacting a vaporous mixture containing ethanol and hydrogen with a dehydrogenation catalyst in a dehydrogenation zone maintained under dehydrogenation conditions effective for dehydrogenation of ethanol to yield ethyl acetate.

Typical dehydrogenation conditions include use of an ethanol:hydrogen molar ratio of from about 1:10 to about 1000:1, a combined partial pressure of ethanol and hydrogen of up to about 50 bar ($5 \times 10^6$ Pa), and a temperature in the range of from about 100° C. to about 260° C.

Preferably the combined partial pressure of ethanol and hydrogen ranges from about 3 bar ($3 \times 10^5$ Pa) up to about 50 bar ($5 \times 10^6$ Pa), and is more preferably at least 6 bar ($6 \times 10^5$ Pa) up to about 30 bar ($3 \times 10^6$ Pa), and even more preferably in the range of from about 10 bar ($10^6$ Pa) up to about 20 bar ($3 \times 10^6$ Pa), for example from about 12 bar ($1.2 \times 10^6$ Pa) to about 15 bar ($1.5 \times 10^6$ Pa).

Dehydrogenation is preferably conducted in the dehydrogenation zone at a temperature of from about 200° C. to about 250° C., preferably at a temperature in the range of from about 210° C. to about 240° C., even more preferably at a temperature of about 220° C.

The ethanol:hydrogen molar ratio in the vaporous mixture fed into contact with the dehydrogenation catalyst usually will not exceed about 400:1 or about 500:1 and may be no more than about 50:1.

The dehydrogenation catalyst is desirably a catalyst containing copper, optionally in combination with chromium, manganese, aluminium, zinc, nickel or a combination of two or more of these metals, such as a copper, manganese and aluminium containing catalyst. Preferred catalysts comprise, before reduction, copper oxide on alumina, an example of which is the catalyst sold by Mallinckrodt Specialty Chemicals, Inc., under the designation E408Tu, a catalyst which contains 8% by weight of alumina. Other preferred catalysts include chromium promoted copper catalysts available under the designations PG85/1 (Kvaerner Process Technology Limited) and CU0203T (Engelhard), manganese promoted copper catalysts sold under the designation T4489 (Sud Chemie AG), and supported copper catalysts sold under the designation D-32-J (Sud Chemie AG). E408Tu is a particularly preferred dehydrogenation catalyst.

In the dehydrogenation step the rate of supply of the $C_2$ feedstock to the dehydrogenation zone typically corresponds to an ethanol liquid hourly space velocity (LHSV) of from about 0.5 hr$^{-1}$ to about 1.0 hr$^{-1}$.

Hydrogen is produced as a result of the dehydrogenation reaction and can be recycled to the dehydrogenation zone from downstream in the process. The hydrogen can be substantially pure hydrogen or can be in the form of a mixture with other gases that are inert to the $C_2$ feedstock and to the dehydrogenation catalyst. Examples of such other gases include inert gases such as nitrogen, methane and argon.

In the dehydrogenation zone, side reactions may also occur, including formation of water. It is postulated that such side reactions include formation of acetaldehyde which in turn can undergo aldol formation, followed by dehydration to form an unsaturated alcohol and water. These reactions can be summarised thus:

$$CH_3CH_2OH = CH_3CHO + H_2 \qquad (5)$$

$$2CH_3CHO = CH_3CH(OH)CH_2CHO \qquad (6) \text{ and}$$

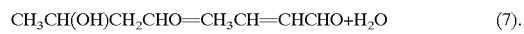

$$CH_3CH(OH)CH_2CHO = CH_3CH = CHCHO + H_2O \qquad (7).$$

The crotonaldehyde produced by equation (7) can then undergo hydrogenation to form 2-butanol thus:

$$CH_3CH = CHCHO + H_2 = CH_3CH_2CH_2CH_2OH \qquad (8).$$

Other side reactions which release water as a by-product include formation of ketones, such as acetone and butan-2-one, and formation of ethers, such as diethyl ether.

It is alternatively possible to subject the $C_2$ feedstock to oxidation in order to effect production of ethyl acetate as taught by U.S. Pat. No. 5,334,751 or by U.S. Pat. No. 4,996,007.

Alternatively the $C_2$ feedstock can be passed in admixture with air over a palladium on a silica carrier catalyst thereby to produce ethyl acetate by direct oxidation of ethanol with air as taught by BR-A-91/04652.

Yet another method of effecting oxidation of the $C_2$ feedstock so as to produce ethyl acetate is to use bromous acid or a salt thereof in acid medium as described in JP-A-59/025334.

Yet another method of converting the $C_2$ feedstock to ethyl acetate is to react it with acetaldehyde to yield ethyl acetate and hydrogen according to equation (4) above.

Still another method of converting the $C_2$ feedstock to ethyl acetate involves oxidation of ethanol to acetaldehyde, for example by the process of U.S. Pat. No. 4,220,803, followed by conversion of the acetaldehyde product to ethyl acetate by the Tischenko reaction of equation (2) above.

Typical Tischenko reaction conditions are set out in U.S. Pat. No. 3,714,236. Again water can be a by-product of this reaction, being formed, it is postulated, by equations (6) and (7) above.

In step (b) of the process of the invention there is recovered from the ethyl acetate production zone an intermediate reaction product mixture comprising hydrogen and liquefiable products comprising ethyl acetate, ethanol, water, and by-products containing reactive carbonyl groups. This step can be effected in any convenient manner and may include a condensation step in order to condense liquefiable products present in the intermediate reaction product mixture. Alternatively the intermediate reaction product can be passed directly to step (c) without any intermediate condensation step.

A range of undesirable by-products may be present in the intermediate reaction product mixture, some of which would cause separation problems if the intermediate reaction product mixture were to be directly refined because their boiling points are close to that of ethyl acetate or because they form azeotropes with ethyl acetate whose boiling point is close to that of ethyl acetate. Such by-products may be present in the $C_2$ feedstock or may be produced in step (c). Problematical by-products are aldehydes and ketones, such as n-butyraldehyde and butan-2-one. In order to avoid problems due to the presence of such by-products in the distillation step (e), even in amounts as small as about 0.1 mol % or less, e.g. about 0.01 mol % or less, the problematical by-products are substantially removed as a result of the selective hydrogenation step (c). Accordingly, liquefiable products present in the intermediate reaction product mixture of step (b) are reacted in step (c) with hydrogen over a suitable selective hydrogenation catalyst. The catalyst type and reaction conditions are chosen so that aldehydes and ketones are hydrogenated to their respective alcohols, while hydrogenation of ethyl acetate is minimal. Among aldehyde and ketone by-products which may be present, butan-2-one and n-butyraldehyde, in particular, would otherwise cause problems in any subsequent distillation. These compounds are hydrogenated in the selective hydrogenation zone in step (c) to the corresponding alcohols, i.e. 2-butanol and n-butanol respectively, which can be readily separated from ethyl acetate by distillation.

The mixture supplied to the selective hydrogenation zone in step (c) contains, in addition to ethanol, hydrogen either alone or in admixture with one or more inert gases that are inert to the reactants and catalysts in the selective hydrogenation step (c) of the process of the invention. Examples of such inert gases have been given above. The source of the hydrogen used in the selective hydrogenation step (c) may be hydrogen formed in the dehydrogenation step and may include gas recycled from the downstream end of the selective hydrogenation zone.

The selective hydrogenation step (c) is typically conducted at a temperature of from about 20° C. to about 160° C., preferably at a temperature in the range of from about 40° C. to 120° C., even more preferably at a temperature of about 60° C. to about 80° C. Typical selective hydrogenation conditions include use of a reaction product mixture:hydrogen molar ratio of from about 1000:1 to about 1:1, preferably from about 100:1 to about 5:1, for example about 20:1.

The combined partial pressure of liquefiable products and hydrogen in the selective hydrogenation zone typically lies in the range of from about 5 bar ($5 \times 10^5$ Pa) up to about 80 bar ($8 \times 10^6$ Pa), and is even more typically from about 25 bar ($2.5 \times 10^6$ Pa) to about 50 bar ($5 \times 10^6$ Pa).

The selective hydrogenation catalyst used in step (c) of the process of the invention is selected to have good activity for hydrogenation of reactive carbonyl containing compounds, but relatively poor ester hydrogenation activity. Suitable catalysts comprise metals selected from nickel, palladium and platinum. Ruthenium, supported on carbon, alumina or silica is also effective, as are other metal catalysts such as rhodium and rhenium. Preferred catalysts include nickel on alumina or silica and ruthenium on carbon. Particularly preferred catalysts include 5% ruthenium on carbon available from Engelhard.

The rate of supply of liquefiable liquid products of the intermediate reaction product mixture to the selective hydrogenation zone depends upon the activity of the selective hydrogenation catalyst but typically corresponds to a liquid hourly space velocity (LHSV) of from about 0.1 hr$^{-1}$ to about 2.0 hr$^{-1}$, preferably from about 0.2 hr$^{-1}$ to about 1.5 hr$^{-1}$. When using, for example, a ruthenium on carbon catalyst the LHSV may be from about 0.5 hr$^{-1}$ to about 2.0 hr$^{-1}$, for example from about 1.0 hr$^{-1}$ to about 1.5 hr$^{-1}$. When using a nickel containing catalyst the LHSV may be, for example, from about 0.3 hr$^{-1}$ to about 0.5 hr$^{31\ 1}$.

Step (d) of the process of the present invention comprises recovering from the selective hydrogenation zone a selectively hydrogenated reaction product mixture comprising ethyl acetate, ethanol, hydrogen and hydrogenated by-products. Typically this includes a condensation step in order to separate liquefiable materials from a gaseous stream containing unreacted hydrogen which can be recycled for dehydrogenation or for selective hydrogenation.

Step (e) of the process of the invention comprises distilling material of the selectively hydrogenated reaction product mixture in one or more distillation zones so as to produce a first composition comprising substantially pure ethyl acetate and a second composition comprising ethanol and water. In this step the material subjected to distillation typically has a water content of less than about 20 mol %, more usually not more than about 15 mol %.

Ethanol, water and ethyl acetate form a minimum boiling ternary azeotrope upon distillation thereof.

Step (e) may comprise an extractive distillation procedure as described in U.S. Pat. No. 4,569,726 or in U.S. Pat. No. 4,379,028.

Preferably, however, distillation is carried in step (e) by a procedure which takes advantage of the fact that the composition of the minimum boiling ternary azeotrope formed by ethanol, water and ethyl acetate depends upon the pressure at which distillation is effected. Hence a preferred distillation procedure comprises supplying material of the selectively hydrogenated reaction product mixture to a first distillation zone maintained under distillation conditions effective for distillation therefrom of a first distillate comprising ethyl acetate, ethanol, and water, recovering a first distillate comprising ethyl acetate, ethanol, and water from the first distillation zone and a bottom product comprising ethanol and water, supplying material of the first distillate to a second distillation zone maintained under distillation conditions effective for distillation therefrom of a second distillate comprising ethanol, water, and ethyl acetate (typically a minor amount of ethyl acetate) and so as to yield a substantially pure ethyl acetate bottom product, and recovering a substantially pure ethyl acetate bottom product from the second distillation zone. The first distillation zone is preferably operated at a pressure less than about 4 bar ($4 \times 10^5$ Pa), preferably from about 1 bar ($10^5$ Pa) up to about 2 bar ($2 \times 10^5$ Pa), while the second distillation zone is operated at a higher pressure than that of the first distillation zone, for example at a pressure of from about 4 bar ($4 \times 10^5$ Pa) to about 25 bar ($2.5 \times 10^6$ Pa), preferably from about 9 bar ($9 \times 10^5$ Pa) to about 15 bar ($15 \times 10^5$ Pa).

It can be shown that in this preferred distillation procedure the rate of flow of the first distillate from the first distillation zone to the second distillation zone and the corresponding flow rate from the second distillation zone to the first distillation zone of the second distillate can be minimised by operating one of the distillation zones so that the distillate has a composition very close to that of the ternary azeotrope at that pressure. However, in order to operate that zone so that the distillate has a composition close to that of the ternary azeotrope at its pressure of operation, a high degree of separation is required which necessitates use of a column with many distillation trays and a high heat input. In addition, since water has the highest latent heat of vaporisation out of the three components of the ternary azeotrope, the total heat input to the two zones can be minimised by minimising the water content of the feeds to the distillation zones.

In addition to forming a ternary azeotrope, the three components of the ternary azeotrope can also form binary azeotropes with one of the other components. For example, ethanol forms a binary azeotrope with water and also with ethyl acetate. It is preferred to select a pressure of operation of the second distillation zone so that the binary azeotrope between ethanol and ethyl acetate at that pressure has a lower ethyl acetate content than the ternary azeotrope at that pressure and further to select a pressure of operation for the first distillation zone and to adjust the flow rates of the distillates between the first and second zones so that the first distillate has as low a water content as possible. In this way the second distillate recovered from the second distillation zone will have a low content of ethyl acetate.

In the preferred distillation procedure an ethanol rich stream containing substantially all of the water in the selectively hydrogenated reaction product mixture is recovered from the bottom of the first distillation zone, while an overhead stream that contains "light" components present in the selectively hydrogenated reaction product mixture is recovered from the first distillation zone, and the first distillate comprises a liquid draw stream which is recovered from an upper region of the first distillation zone and which comprises ethyl acetate, ethanol, water and minor amounts of other components. By the term "light" components is meant components that have lower boiling points than ethyl acetate and its azeotropes with water and ethanol. The liquid draw stream typically contains less than about 10 mol % water. For example, it suitably comprises from about 1 mol % to about 6 mol % water, from about 40 mol % to about 55 mol % ethyl acetate, not more than about 2 mol % minor products (preferably not more than about 1 mol % minor products) and the balance ethanol. Thus it may typically contain about 45 mol % ethyl acetate, about 50 mol % ethanol, about 4 mol % water and about 1 mol % other components. This liquid draw stream is passed to the second distillation zone. The second distillate, with a typical composition of about 25 mol % ethyl acetate, about 68 mol % ethanol, about 6 mol % water, and about 1 mol % other components, is recovered as an overhead stream from the second distillation zone, while a bottom product comprising ethyl acetate is recovered from the second distillation zone which typically contains from about 99.8 mol % to about 99.95 mol % ethyl acetate; this second distillate is returned to the first distillation zone, preferably at a point above the feed point of the liquefiable products of the selectively hydrogenated reaction product mixture.

The overhead stream from the first distillation zone contains "light" components present in the intermediate reaction product mixture, such as diethyl ether, acetaldehyde and acetone. It can be burnt as a fuel.

In step (f) of the process of the invention the ethanol rich stream recovered from the bottom of the first distillation zone is subjected to treatment for the removal of water therefrom thereby to produce a relatively dry ethanol stream which is suitable for recycle to step (a), if desired. This ethanol rich stream will contain any "heavies", i.e. products, including unknown products, with high boiling points compared to those of ethanol and ethyl acetate. These can be separated from the ethanol and water by distillation, if desired, prior to effecting removal of water from the resulting distillate. One suitable method for removal of water from the ethanol rich stream or from the distillate resulting from "heavies" removal is molecular sieve adsorption. Azeotropic distillation with a suitable entrainment agent, such as benzene or cyclohexane, can alternatively be used. Membranes are currently under development which will enable separation of water from ethanol; these are reported to be nearly ready for commercial exploitation. Hence use of a membrane is another option available for separating water from the ethanol rich stream.

Preferably the water content of the relatively dry ethanol produced in step (f) is less than about 5 mol %, and preferably less than about 2 mol %.

BRIEF DESCRIPTION OF THE DRAWINGS

In order that the invention may be clearly understood and readily carried into effect, a preferred form of plant for the production of ethyl acetate, and a process in accordance with the invention will now be described, by way of example only, with reference to the accompanying drawings, wherein:

FIGS. 2 and 3 are triangular diagrams illustrating the boiling behaviour of ternary mixtures of ethanol, water and ethyl acetate at two different pressures.

Referring to FIG. 1 of the drawings, it will be appreciated by those skilled in the art that, since the drawing is diagrammatic, many conventional items of equipment, such as pumps, surge drums, flash drums, heat exchangers, temperature controllers, pressure controllers, holding tanks, temperature gauges, pressure gauges, and the like, which would be required in an operating plant, have been omitted for the sake of simplicity. Such items of equipment would be incorporated in an actual plant in accordance with standard chemical engineering practice and form no part of the present invention. Moreover there are many ways of effecting heat exchange and the depiction of separate heat exchangers each with its own heating or cooling line does not necessarily mean that single heat exchanger units are necessary. Indeed in many cases it may be more practicable and economic to use two separate heat exchangers instead of one with a step change in temperature occurring in each. It is also practicable to use conventional heat recovery techniques so as to recover heat from, or to increase the temperature of, one stream by heat exchange with another stream of the plant.

Figure 1:
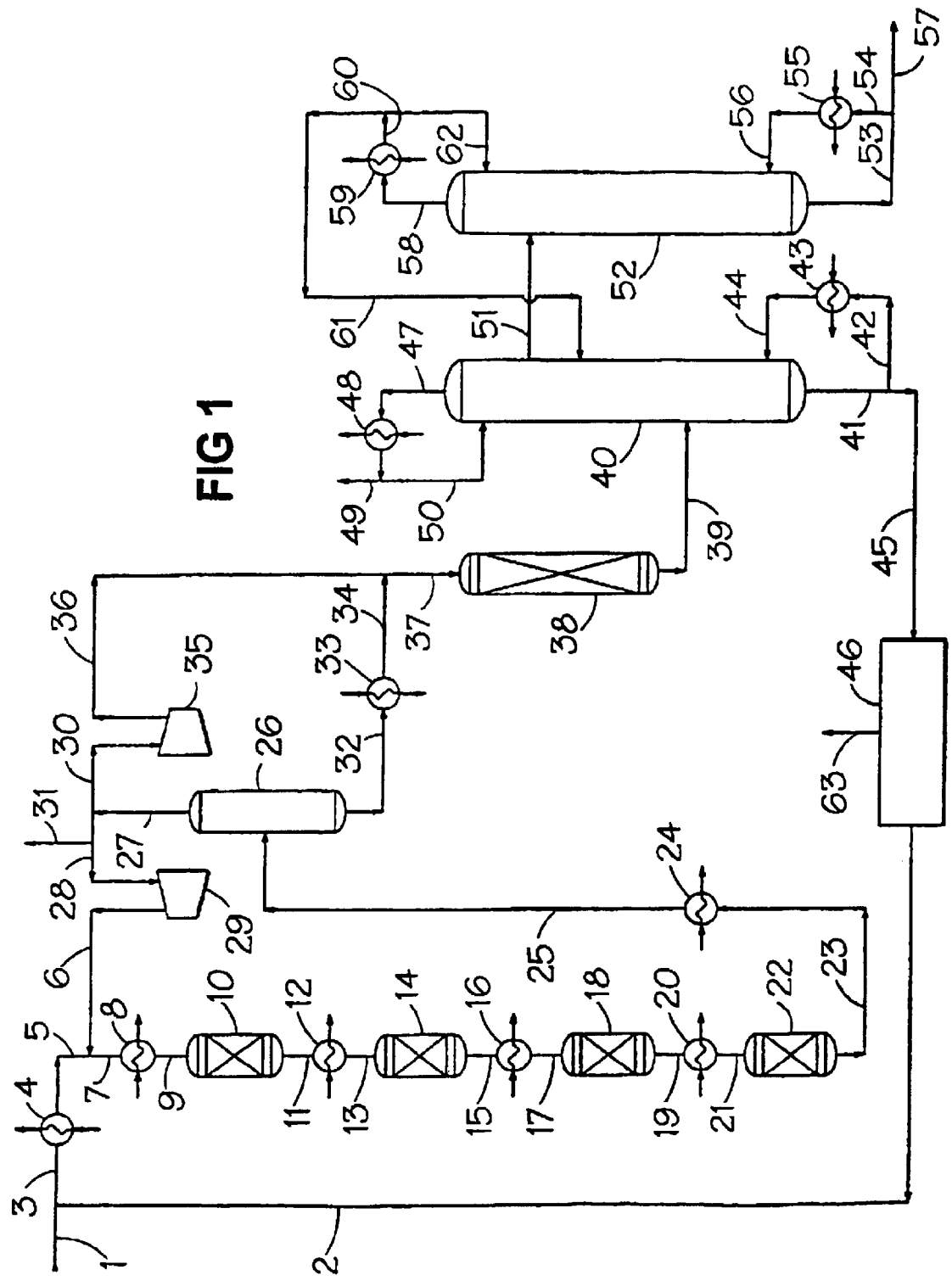
FIG. 1 is a flow diagram of a plant for the production of ethyl acetate constructed to operate a process in accordance with the invention.

In the plant of FIG. 1 a stream of crude ethanol is pumped to the plant from a suitable holding tank (not shown) in line 1 at a pressure of 16.2 bar absolute ($16.2 \times 10^5$ Pa) and at a temperature of approximately 30° C. and is admixed with recycled material from line 2. The resulting mixture in line 3 is heated by means of heat exchanger 4 to a temperature of 166° C. thereby forming a vaporous stream which passes on in line 5 to be mixed with a stream of hydrogen from line 6. The resulting mixture passes on in line 7, is superheated in superheater 8 using high pressure steam, and exits it in line 9 at a pressure of 14.8 bar absolute ($14.8 \times 10^5$ Pa) and at a temperature of 235° C. Line 9 leads to a first dehydrogenation reactor 10 which contains a charge of a reduced copper oxide catalyst. A suitable catalyst is that sold under the designation E408Tu by Mallinckrodt Specialty Chemicals, Inc. In passage through first dehydrogenation reactor 10 the mixture of ethanol and hydrogen is partly converted by dehydrogenation according to equation (3) above to form ethyl acetate. This dehydrogenation reaction is endothermic.

The first intermediate dehydrogenation mixture exits reactor 10 in line 11 at a temperature in the range of from 205° C. to 220° C. and is reheated in heater 12 under the influence of high pressure steam. The reheated mixture flows on in line 13 to a second dehydrogenation reactor 14 which also contains a charge of the same dehydrogenation catalyst as that in reactor 10. Further dehydrogenation of ethanol to ethyl acetate occurs in passage through second dehydrogenation reactor 14.

A second intermediate dehydrogenation mixture containing ethyl acetate, unreacted ethanol and hydrogen exits reactor 14 in line 15 and is reheated in reheater 16 which is heated by means of high pressure steam. The reheated stream flows on in line 17 to a third dehydrogenation reactor 18 which contains a charge of the same dehydrogenation catalyst as is present in reactors 10 and 14.

The resulting third intermediate reaction mixture flows on in line 19 to heat exchanger 20 which is also heated by means of high pressure steam. The reheated mixture passes on in line 21 to fourth dehydrogenation reactor 22 which contains a further charge of the same dehydrogenation catalyst that is loaded into the first, second and third dehydrogenation reactors 10, 14, and 18.

A crude product mixture exits fourth dehydrogenation reactor 22 in line 23, is cooled in passage through a heat exchanger 24, and emerges in line 25 at a temperature of 60° C. and at a pressure of 11.3 bar ($11.3 \times 10^5$ Pa) absolute.

The crude product mixture in line 25 comprises hydrogen, ethyl acetate, unconverted ethanol, water and minor amounts of impurities present either from contamination in the feed or recycle streams or from side reactions in reactors 10, 14, 18 and 22. Examples of these impurities include iso-propanol, acetaldehyde, diethyl ether, methanol, acetone, di-iso-propyl ether, n-butyraldehyde, butan-2-one, sec-butanol, iso-propyl acetate, pentan-2-one, n-butanol, sec-pentanol, sec-butyl acetate, ethyl butyrate, n-butyl acetate and di-n-butyl ether. Of particular significance in relation to this invention are those impurities whose boiling points are close to that of ethyl acetate or which form azeotropic mixtures with ethyl acetate. These include ethanol, as well as certain carbonyl-containing compounds such as acetone, acetaldehyde and butan-2-one.

The crude mixture in line 25 flows into a knockout pot 26 which is provided with a condenser (not shown) supplied with chilled coolant. The uncondensed gases, which are now at a temperature of −10° C., are recovered in line 27. A part of these gases is recycled in line 28 and compressed by means of gas recycle compressor 29 to a pressure of 15.5 bar ($1.55 \times 10^6$ Pa) absolute to form the gas stream in line 6 for supply to the first dehydrogenation reactor 10. Another part is taken in line 30 for a purpose which will be described hereunder. A purge stream is taken in line 31.

The condensate is removed from knockout pot 26 in line 32 and is pumped by a pump (not shown) to heat exchanger 33. The resulting re-heated liquid, now at a temperature of 60° C. to 80° C., is fed via line 34 and mixed with a hydrogen-containing gas which is at a temperature of 119° C. and has been compressed by a second gas compressor 35 to a pressure of 43.1 bar ($4.31 \times 10^6$ Pa) absolute so as to pass along line 36. The resulting mixture flows on in line 37 into a reactor 38 which contains a charge of a selective hydrogenation catalyst which is chosen so as selectively to hydrogenate reactive carbonyl-containing compounds, such as n-butyraldehyde, butan-2-one and the like, to the respective corresponding alcohols but not to effect any significant hydrogenation of ethyl acetate to ethanol. The inlet temperature to reactor 37 is adjusted as necessary to a temperature in the range of from 60° C. to 80° C. in dependance upon the degree of deactivation of the catalyst but is chosen to be as low as possible consistent with obtaining an acceptable reaction rate because the equilibrium is favourable at lower temperatures than at high temperatures. A preferred catalyst is 5% ruthenium on carbon available from Engelhard.

The resulting selectively hydrogenated reaction product is now essentially free from reactive carbonyl compounds, such as aldehydes and ketones, and exits reactor 38, in admixture with unreacted hydrogen, in line 39 at a temperature of 70° C. to 90° C. This line leads to a lower part of a first distillation column 40 which is maintained at a is pressure of 1.5 bar ($1 \times 10^5$ Pa) absolute. A bottoms product is withdrawn from distillation column 40 in line 41. Part of this is recycled to distillation column through line 42, column reboiler 43 and line 44. The remainder is passed by way of line 45 to a purification section (or water removal package) 46 in which it is treated in any convenient manner for the removal of water (and possibly other impurities) therefrom so as to yield a stream of moderately dry ethanol for recycle to the first dehydrogenation reactor 10 by way of line 2. The precise design of water removal package 46 will depend upon the composition of the ethanol feed stream in line 1. The bottoms product in line 41 typically comprises mainly ethanol with minor amounts of, for example, iso-propanol, water, $C_{4+}$ alkanols, and traces of ketones, other esters and ethers.

An overhead stream, which typically comprises a major proportion of diethyl ether and lesser amounts of other ethers, methanol, ethanol, n-butyraldehyde, and alkanes, as well as traces of acetaldehyde, ethyl acetate, and water, is recovered in line 47 and condensed by means of condenser 48. Uncondensed gases are purged in line 49, while the resulting condensate is recycled to the top of distillation column 38 as a reflux stream in line 50. A side draw stream is taken from distillation column 40 in line 51 and pumped by a pump (not shown) to a second distillation column 52 which is maintained at an overhead pressure of 12 bar ($1.2 \times 10^6$ Pa) absolute.

From the bottom of distillation column 52 a stream comprising substantially pure ethyl acetate is recovered in line 53, part of which is recycled to a lower part of distillation column 52 by way of line 54, column reboiler 55, and line 56. The remainder forms the product stream in line 57 from the plant; this can be taken to storage or further distilled in one or more further distillation columns, if desired, in order to remove minor amounts of iso-propyl acetate, di-propyl ether, and 1-ethoxybutane.

An overhead product consisting mainly of ethanol, ethyl acetate and water, besides smaller amounts of 1-ethoxybutane, methanol, diethyl ether and di-propyl ether and traces of alkanes, is taken in line 58 and condensed by means of condenser 59. The resulting condensate passes on in line 60, some being recycled to the first distillation column by way of line 61 while the remainder is recycled as a reflux stream to the second distillation column 52 in line 62. Reference numeral 63 indicates a line for recovery of water and other materials from water removal package 46.

The compositions in mol % of some of the more important streams in the plant of FIG. 1 are set out in Table 1 below.

At start-up a charge of 200 ml of a tabulated copper oxide catalyst available under the designation E408Tu from Mallinckrodt Specialty Chemicals was placed in the reactor which was then purged with nitrogen at 14.5 bar ($14.5 \times 10^5$ Pa). A dilute $H_2$ in $N_2$ gaseous mixture at 3 bar ($3 \times 10^5$ Pa) was passed over the catalyst at a rate of 600 standard liters per hour for 60 hours in order to effect catalyst reduction.

TABLE 1

| Stream | 1 | 2 | 9 | 25 | 27 | 32 | 37 | 39 | 45 | 49 | 51 | 57 | 61 | 63 |
|---|---|---|---|---|---|---|---|---|---|---|---|---|---|---|
| Hydrogen | 0.00 | 0.00 | 1.96 | 32.43 | 95.67 | 0.24 | 5.32 | 3.26 | 0.00 | 64.41 | 0.00 | 0.00 | 0.00 | 0.00 |
| Carbon monoxide | 0.00 | 0.00 | 0.01 | 0.17 | 0.49 | 0.00 | 0.03 | 0.03 | 0.00 | 0.64 | 0.00 | 0.00 | 0.00 | 0.00 |
| Water | 0.13 | 0.13 | 0.13 | 1.20 | 0.04 | 1.80 | 1.71 | 1.73 | 2.26 | 0.93 | 3.94 | 0.00 | 5.36 | 39.80 |
| Methanol | 0.01 | 0.00 | 0.01 | 0.01 | 0.00 | 0.01 | 0.01 | 0.01 | 0.00 | 0.20 | 0.06 | 0.00 | 0.09 | 0.00 |
| Ethanol | 99.84 | 99.84 | 97.82 | 49.25 | 1.39 | 73.50 | 69.67 | 72.70 | 96.52 | 16.76 | 50.42 | 0.02 | 68.73 | 37.90 |
| Ethyl acetate | 0.00 | 0.00 | 0.01 | 15.03 | 0.91 | 22.32 | 21.18 | 20.86 | 0.00 | 7.17 | 45.40 | 99.98 | 25.57 | 0.00 |
| Acetaldehyde | 0.00 | 0.00 | 0.00 | 0.51 | 0.03 | 0.75 | 0.71 | 0.01 | 0.00 | 0.13 | 0.14 | 0.00 | 0.19 | 0.00 |
| Ethane | 0.00 | 0.00 | 0.00 | 0.09 | 0.20 | 0.03 | 0.04 | 0.04 | 0.00 | 0.82 | 0.00 | 0.00 | 0.00 | 0.00 |
| Methane | 0.00 | 0.00 | 0.03 | 0.41 | 1.17 | 0.03 | 0.09 | 0.09 | 0.00 | 1.78 | 0.00 | 0.00 | 0.00 | 0.00 |
| Di-ethyl ether | 0.01 | 0.00 | 0.01 | 0.27 | 0.09 | 0.37 | 0.35 | 0.36 | 0.00 | 7.09 | 0.04 | 0.00 | 0.06 | 0.00 |
| n-butyraldehyde | 0.00 | 0.00 | 0.00 | 0.01 | 0.00 | 0.01 | 0.01 | 0.00 | 0.00 | 0.00 | 0.00 | 0.00 | 0.00 | 0.00 |
| n-butanol | 0.00 | 0.01 | 0.00 | 0.12 | 0.00 | 0.18 | 0.17 | 0.19 | 0.25 | 0.01 | 0.00 | 0.00 | 0.00 | 4.53 |
| sec-butanol | 0.00 | 0.01 | 0.00 | 0.26 | 0.00 | 0.38 | 0.36 | 0.51 | 0.67 | 0.05 | 0.00 | 0.00 | 0.00 | 12.15 |
| Butan-2-one | 0.01 | 0.00 | 0.01 | 0.10 | 0.01 | 0.14 | 0.14 | 0.00 | 0.00 | 0.00 | 0.00 | 0.00 | 0.00 | 0.00 |
| n-butyl acetate | 0.00 | 0.00 | 0.00 | 0.05 | 0.00 | 0.08 | 0.07 | 0.07 | 0.10 | 0.01 | 0.00 | 0.00 | 0.00 | 1.81 |
| sec-butyl acetate | 0.00 | 0.00 | 0.00 | 0.02 | 0.00 | 0.03 | 0.03 | 0.03 | 0.04 | 0.00 | 0.00 | 0.00 | 0.00 | 0.73 |
| Ethyl butyrate | 0.00 | 0.00 | 0.00 | 0.04 | 0.00 | 0.07 | 0.06 | 0.06 | 0.09 | 0.00 | 0.00 | 0.00 | 0.00 | 1.63 |
| Di-butyl ether | 0.00 | 0.00 | 0.00 | 0.00 | 0.00 | 0.01 | 0.01 | 0.01 | 0.01 | 0.00 | 0.00 | 0.00 | 0.00 | 0.18 |
| n-hexanol | 0.00 | 0.00 | 0.00 | 0.00 | 0.00 | 0.00 | 0.00 | 0.00 | 0.01 | 0.00 | 0.00 | 0.00 | 0.00 | 0.18 |
| iso-butanol | 0.00 | 0.01 | 0.01 | 0.01 | 0.00 | 0.01 | 0.01 | 0.01 | 0.01 | 0.00 | 0.00 | 0.00 | 0.00 | 0.18 |
| Others | 0.00 | 0.00 | 0.00 | 0.02 | 0.00 | 0.04 | 0.03 | 0.03 | 0.04 | 0.00 | 0.00 | 0.00 | 0.00 | 0.91 |
| Total | 100.00 | 100.00 | 100.00 | 100.00 | 100.00 | 100.00 | 100.00 | 100.00 | 100.00 | 100.00 | 100.00 | 100.00 | 100.00 | 100.00 |

FIG. 2 is a triangular diagram illustrating the distillation characteristics of mixtures of ethanol, water and ethyl acetate at 760 mm Hg ($1.01 \times 10^6$ Pa) in which are plotted distillation lines for different mixtures of the three components. FIG. 3 is a similar diagram illustrating the distillation characteristics of the same ternary system at 9308 mm Hg ($12.41 \times 10^6$ Pa). It will be noted that there are significant differences between the distillation lines observed at different operating pressures. In FIG. 2 the composition of a typical feed as might be supplied in line 39 of the plant of FIG. 1 is indicated by point A. Point B indicates the composition of the side draw stream in line 51 for this feed. Point C indicates the composition of the resulting bottom stream in line 41 and point D indicates the composition of the stream in line 61. The effective feed composition to column 40 lies on the intersection of the straight line joining A and D with the straight line joining points B and C. In FIG. 3 the points B and D represents the same compositions as the corresponding points in the triangular diagram of FIG. 2. Point E represents the composition of the substantially pure ethyl acetate recovered in line 45.

The invention is further described in the following Examples.

EXAMPLES 1 to 5

These Examples investigated the dehydrogenation of ethanol to ethyl acetate in the presence of hydrogen. The apparatus used included a dehydrogenation reactor made of stainless steel tubing which contained a charge of reduced copper oxide catalyst and which was immersed in a hot oil bath for heating purposes.

The oil bath was raised to the temperature indicated in Table 2 below. The gas feed was then changed to pure hydrogen.

In operation hydrogen was introduced to the dehydrogenation reactor at a rate of 2 standard liters per hour by way of a pressure regulator and flow controller through a line which was immersed in the bottom of the oil bath. An ethanol stream whose composition is set out in Table 2 was fed as a liquid at a rate of 200 ml/hr to a vaporiser and mixed with the hydrogen. The resulting vaporous mixture of ethanol and hydrogen was supplied to the dehydrogenation reactor.

The reaction products were cooled and the liquid condensate was analysed by gas chromatography. The results obtained are summarised in Table 2.

TABLE 2

| Example No | Feed | 1 | 2 | 3 | 4 | 5 |
|---|---|---|---|---|---|---|
| Temperature (° C.) | — | 225 | 224 | 224 | 223 | 224 |
| Pressure (bar)[$10^5$ Pa] | — | 4.53 | 2.74 | 7.91 | 28.6 | 47.0 |
| Product Analysis (wt %) | | | | | | |
| Acetaldehyde | 0.007 | 2.578 | 5.317 | 1.388 | 0.114 | 0.027 |
| Methanol | 0.064 | 0.063 | 0.087 | 0.034 | 0.013 | 0.011 |
| Di-ethyl ether | 0.108 | 0.133 | 0.120 | 0.139 | 0.167 | 0.185 |
| Ethanol | 95.093 | 63.184 | 66.778 | 64.050 | 67.236 | 72.676 |
| Acetone | 0.007 | 2.264 | 2.883 | 1.679 | 0.630 | 0.326 |
| iso-propanol | 3.403 | 1.582 | 1.081 | 2.114 | 3.210 | 3.511 |

TABLE 2-continued

| Example No | Feed | 1 | 2 | 3 | 4 | 5 |
|---|---|---|---|---|---|---|
| Di-iso-propyl ether | 0.116 | 0.139 | 0.134 | 0.138 | 0.136 | 0.138 |
| n-butyraldehyde | 0 | 0.012 | 0.010 | 0.006 | 0.004 | 0.005 |
| Ethyl acetate | 0.030 | 25.605 | 18.935 | 27.087 | 26.377 | 21.107 |
| Butan-2-one | 0.005 | 1.230 | 1.655 | 0.661 | 0.074 | 0.015 |
| sec-butanol | 0.004 | 0.768 | 0.543 | 0.761 | 0.360 | 0.174 |
| iso-propyl acetate | 0 | 0.184 | 0.144 | 0.040 | 0.316 | 0.318 |
| Pentan-2-one | 0 | 0.316 | 0.309 | 0.233 | 0.055 | 0.010 |
| n-butanol | 0.097 | 0.329 | 0.410 | 0.274 | 0.203 | 0.431 |
| sec-pentanol | 0 | 0.138 | 0.075 | 0.180 | 0.148 | 0.087 |
| sec-butyl acetate | 0 | 0.058 | 0.037 | 0.057 | 0.052 | 0.044 |
| Ethyl butyrate | 0 | 0.132 | 0.115 | 0.093 | 0.030 | 0.075 |
| n-butyl acetate | 0 | 0.123 | 0.096 | 0.086 | 0.022 | 0.076 |
| Water | 0.540 | 0.789 | 0.920 | 0.660 | 0.450 | 0.460 |
| Others | 0.526 | 0.373 | 0.351 | 0.320 | 0.403 | 0.324 |
| Total | 100.00 | 100.00 | 100.00 | 100.00 | 100.00 | 100.00 |

EXAMPLES 6 to 9

In these Examples the selective hydrogenation of reactive carbonyl compounds in the presence of ethyl acetate was investigated using a hydrogenation reactor constructed out of stainless steel which was immersed in a hot oil bath for heating purposes.

In operation hydrogen was introduced by way of a pressure regulator and flow controller to the reactor which contained a charge of an Englehard 5% ruthenium on carbon granular catalyst.

At start up a charge of 100 ml of the granular catalyst was placed in the reactor which was then supplied with hydrogen at a pressure of 7.9 bar ($7.9 \times 10^5$ Pa), and warmed to 180–200° C. from room temperature at a rate of 20° C per hour. The reactor was held at 180–200° C. for one hour and then cooled. At the end of this procedure the catalyst was fully reduced.

Dehydrogenation reaction product mixture whose composition is set out under "Feed" in Table 3 was introduced to a heater at a rate of 130 ml/hr and admixed with 7.8 standard liters per hour of hydrogen prior to admission to the selective hydrogenation reactor. The reaction product was cooled and the liquid condensate was analysed by gas chromatography. The results are summarised in Table 3.

TABLE 3

| Example No | Feed | 6 | 7 | 8 | 9 |
|---|---|---|---|---|---|
| Reactor Temperature (° C.) | — | 91 | 80 | 72 | 110 |
| Pressure (bar)[$10^5$ Pa] | — | 14.2 | 14.2 | 14.4 | 14.1 |
| Product Analysis (Wt %) | | | | | |
| Acetaldehyde | 0.904 | 0.034 | 0.040 | 0.038 | 0.039 |
| Diethyl ether | 0.579 | 0.428 | 0.418 | 0.417 | 0.419 |
| Ethanol | 68.223 | 70.040 | 70.121 | 70.163 | 70.301 |
| Acetone | 2.282 | trace | trace | trace | trace |
| iso-propanol | 1.004 | 3.232 | 3.233 | 3.213 | 3.231 |
| Di-iso-propyl ether | 0.003 | 0.098 | 0.097 | 0.097 | 0.097 |
| n-butyraldehyde | 0.010 | trace | trace | trace | trace |
| Ethyl acetate | 23.263 | 22.572 | 22.464 | 22.437 | 22.396 |
| Butan-2-one | 0.170 | 0.002 | 0.004 | 0.007 | 0.003 |
| sec-butanol | 0.371 | 0.567 | 0.566 | 0.560 | 0.567 |
| iso-propyl acetate | 0.186 | 0.185 | 0.184 | 0.184 | 0.184 |
| n-butanol | 0.507 | 0.730 | 0.770 | 0.776 | 0.570 |

TABLE 3-continued

| Example No | Feed | 6 | 7 | 8 | 9 |
|---|---|---|---|---|---|
| Water | 1.410 | 1.170 | 1.170 | 1.200 | 1.270 |
| Others | 1.088 | 0.942 | 0.933 | 0.908 | 0.923 |
| Total | 100.00 | 100.00 | 100.00 | 100.00 | 100.00 |

Notes: The increased amount of n-butanol noted in Examples 6 to 9 compared with the amount in the feed can be ascribed not only to n-butanol formed by hydrogenation of n-butyraldehyde present in the feed (the amount of which is, in any case, difficult to measure) but also from hydrogenation of other products which contain $C_4$ groups and which are included in the figure given for "others" in the feed.

EXAMPLES 10 to 12

The general procedure of Examples 6 to 9 was repeated using a different feed and different reaction conditions. The results are set out in Table 4 below.

TABLE 4

| Example No | Feed | 10 | 11 | 12 |
|---|---|---|---|---|
| Reactor Temperature (° C.) | — | 79 | 98 | 119 |
| Pressure (bar) [$10^5$ Pa] | — | 42.6 | 42.1 | 42.5 |
| Product Analysis (Wt %) | | | | |
| Acetaldehyde | 0.952 | 0.006 | 0.006 | 0.006 |
| Diethyl ether | 0.030 | 0.030 | 0.029 | 0.033 |
| Ethanol | 64.703 | 65.930 | 66.034 | 65.627 |
| Acetone | trace | 0 | 0 | 0 |
| iso-propanol | 0.022 | 0.032 | 0.035 | 0.038 |
| n-butyraldehyde | trace | 0 | 0 | 0 |
| Ethyl acetate | 31.692 | 31.410 | 31.155 | 31.409 |
| Butan-2-one | 0.301 | trace | trace | 0.001 |
| sec-butanol | 0.487 | 0.803 | 0.806 | 0.810 |
| n-butanol | 0.560 | 0.588 | 0.596 | 0.573 |
| Water | 0.620 | 0.600 | 0.700 | 0.890 |
| Others | 0.633 | 0.601 | 0.639 | 0.613 |
| Total | 100.00 | 100.00 | 100.00 | 100.00 |

EXAMPLE 13

A mixture containing ethanol, water, ethyl acetate and other components was distilled in a continuous feed laboratory distillation apparatus having the general layout of columns 40 and 52 of FIG. 1, except that line 51 received condensate from line 50, rather than a side draw stream from an outlet positioned somewhat lower in column 40. A bleed of $O_2$-free nitrogen was supplied to column 40 so as to ensure that oxygen was excluded from column 40 in order to prevent oxidation of any oxygen-sensitive components in the feed in line 39 such as aldehydes. Hence column 40 was operated at a few millibars over atmospheric pressure. The feed to column 30 was vaporised in a stream of $O_2$-free nitrogen prior to introduction into column 40. The reflux temperature in column 40 was 64° C., the overhead temperature was 72° C. and the temperature at the bottom of the column was 73° C. The reflux ratio was 5:1. The operating pressure in column 52 was 12.4 bar ($1.24 \times 10^6$ Pa gauge). The overhead temperature was 160° C., the reflux temperature was 153° C. and the boiler temperature was 204° C. The reflux ratio was 2.8:1. The distillation column had 3 thermocouples positioned near the top, at the mid point and near the bottom, the readings of which were 163° C., 180° C. and 180° C. respectively. The results obtained are listed in Table 5 in which amounts are in % by weight.

TABLE 5

| Line No. | 39 | 51 | 41 | 61 | 53 |
|---|---|---|---|---|---|
| Acetaldehyde | 0.009 | 0.007 | 0.013 | 0.446 | |
| Methanol | 0.090 | 0.141 | | 0.199 | |
| Diethyl ether | 0.073 | 0.113 | | 0.226 | |
| Ethanol | 57.626 | 31.077 | 96.579 | 71.382 | 0.064 |
| iso-propanol | 0.027 | | 0.087 | | |
| Ethyl acetate | 40.514 | 68.021 | 0.018 | 24.811 | 99.890 |
| Butan-2-ol | 0.548 | | 1.499 | | |
| n-butanol | 0.192 | 0.021 | 0.519 | | 0.010 |
| Ethyl butyrate | 0.117 | | 0.307 | | |
| Butyl acetate | 0.136 | | 0.358 | | |
| Water | 0.550 | 0.590 | 0.330 | 2.920 | 0.010 |
| "Light" unknowns | 0.020 | 0.029 | | 0.003 | |
| "Heavy" unknowns | 0.098 | 0.001 | 0.290 | 0.013 | 0.026 |
| Total | 100.00 | 100.00 | 100.00 | 100.00 | 100.00 |

What is claimed is:

1. A process for the production of ethyl acetate which comprises:
  (a) converting a $C_2$ feedstock comprising ethanol to ethyl acetate in an ethyl acetate production zone by a procedure selected from:
    (i) dehydrogenation, and
    (ii) reaction with acetaldehyde
  (b) recovering from the ethyl acetate production zone an intermediate reaction product mixture comprising hydrogen and liquefiable products comprising the majority of the ethyl acetate produced in step (a), ethanol, and by-products containing reactive carbonyl groups;
  (c) passing at least a portion of the liquefiable products of the intermediate reaction product mixture as recovered from the ethyl acetate production zone to a selective hydrogenation zone and contacting the liquefiable products of the intermediate reaction product mixture with a selective hydrogenation catalyst in the presence of hydrogen in the selective hydrogenation zone maintained under selective hydrogenation conditions effective to selectively hydrogenate said by-products containing reactive carbonyl groups to corresponding alcohols;
  (d) recovering from the selective hydrogenation zone a selectively hydrogenated reaction product mixture comprising ethyl acetate, ethanol, hydrogen and hydrogenated by-products comprising said corresponding alcohols;
  (e) distilling the selectively hydrogenated reaction product mixture in one or more distillation zones so as to produce a first composition comprising substantially pure ethyl acetate and a second composition comprising ethanol and water;
  (f) treating the second composition of step (e) to separate water therefrom and yield a third composition comprising ethanol with a reduced water content; and
  (g) recovering the third composition of step (f).

2. A process according to claim 1, wherein in step (a) the $C_2$ feedstock is converted to ethyl acetate by a dehydrogenation procedure which comprises contacting a vaporous mixture containing ethanol and hydrogen with a dehydrogenation catalyst in a dehydrogenation zone maintained under dehydrogenation conditions effective for dehydrogenation of ethanol to yield ethyl acetate.

3. A process according to claim 2, wherein the ethanol:hydrogen molar ratio in the dehydrogenation zone is from about 1:10 to about 1000:1, the combined partial pressure of ethanol and hydrogen in the dehydrogenation zone is from about 3 bar ($3 \times 10^5$ Pa) up to about 50 bar ($5 \times 10^6$ Pa), and the temperature in the dehydrogenation zone is from about 100° C. to about 260° C.

4. A process according to claim 3, wherein the combined partial pressure of ethanol and hydrogen in the dehydrogenation zone is at least about 6 bar ($6 \times 10^5$ Pa) up to about 30 bar ($3 \times 10^6$ Pa).

5. A process according to claim 2, wherein the dehydrogenation catalyst is a copper containing catalyst which comprises, before reduction, copper oxide on alumina.

6. A process according to claim 2, wherein the rate of supply of the $C_2$ feedstock to the dehydrogenation zone corresponds to an ethanol liquid hourly space velocity (LHSV) of from about 0.5 hr$^{-1}$ to about 1.0 hr$^{-1}$.

7. A process according to claim 1, wherein the selective hydrogenation conditions in the selective hydrogenation zone of step (c) include a reaction product mixture:hydrogen molar ratio of from about 1000:1 to about 1:1, a combined partial pressure of the liquefiable products of the intermediate reaction product mixture and hydrogen of from about 5 bar ($5 \times 10^5$ Pa) to about 80 bar ($8 \times 10^6$ Pa), and a temperature in the range of from about 20° C. to about 160° C.

8. A process according to claim 1, wherein the combined partial pressure of the liquefiable products of the intermediate reaction product mixture and hydrogen in step (C) is from about 25 bar ($2.5 \times 10^6$ Pa) to about 50 bar ($5 \times 10^6$ Pa).

9. A process according to claim 1, wherein the selective hydrogenation catalyst comprises a metal selected from nickel, palladium, platinum, ruthenium, rhodium and rhenium.

10. A process according to claim 9, wherein the catalyst comprises ruthenium on carbon.

11. A process according to claim 1, wherein the rate of supply of liquefiable liquid products of the intermediate reaction product mixture to the selective hydrogenation zone corresponds to a liquid hourly space velocity (LHSV) of from about 0.5 hr$^{-1}$ to about 2.0 hr$^{-1}$.

12. A process according to claim 1, wherein step (e) comprises supplying the selectively hydrogenated reaction product mixture to a first distillation zone maintained under distillation conditions effective for distillation therefrom of a first distillate comprising ethanol, water and ethyl acetate, recovering a first distillate comprising ethanol, water and ethyl acetate from the first distillation zone and a bottom product comprising ethanol and water, supplying the first distillate to a second distillation zone maintained under distillation conditions effective for distillation therefrom of a second distillate comprising ethanol, water, and ethyl acetate and so as to yield a substantially pure ethyl acetate bottom product, and recovering a substantially pure ethyl acetate bottom product from the second distillation zone.

13. A process according to claim 12, wherein the first distillation zone is operated at a pressure of less than about 4 bar ($4 \times 10^5$ Pa).

14. A process according to claim 12, wherein the first distillation zone is operated at a pressure of from about 1 bar ($10^5$ Pa) to about 2 bar ($2 \times 10^5$ Pa).

15. A process according to claim 12, wherein the second distillation zone is operated at a pressure of from about 4 bar ($4 \times 10^5$ Pa) to about 25 bar ($2.5 \times 10^6$ Pa).

16. A process according to claim 12, wherein the second distillation zone is operated at a pressure of from about 9 bar ($9 \times 10^5$ Pa) to about 15 bar ($1.5 \times 10^6$ Pa).

17. A process according to claim 12, wherein the first distillate contains less than about 10 mol % water.

18. A process according to claim 12, wherein an ethanol rich stream containing substantially all of the water in the selectively hydrogenated reaction product mixture is recovered from the bottom of the first distillation zone, while an overhead stream that contains light components having lower boiling points than ethyl acetate and its azeotropes with water and ethanol present in the selectively hydrogenated reaction product mixture is recovered from the first distillation zone, and in which the first distillate comprises a liquid draw stream which is recovered from an upper region of the first distillation zone and which comprises ethyl acetate, ethanol, water and minor amounts of other components.

19. A process according to claim 18, wherein the liquid draw stream contains from about 40 mol % to about 55 mol % ethyl acetate, from about 1 mol % to about 6 mol % water, not more than about 1 mol % other components, and the balance ethanol.

20. A process according to claim 19, wherein the liquid draw stream contains about 45 mol % ethyl acetate, about 50 mol % ethanol, about 4 mol % water and about 1 mol % other components.

21. A process according to claim 18, wherein the liquid draw stream is passed to the second distillation zone which is operated at a pressure of from about 4 bar ($4 \times 10^5$ Pa) absolute to about 25 bar ($2.5 \times 10^6$ Pa) absolute.

22. A process according to claim 21, wherein the bottom product from the second distillation zone contains from about 99.8 mol % to about 99.95 mol % ethyl acetate.

23. A process according to claim 20, wherein the second distillate comprises the overhead stream from the second distillation zone and is returned to the first distillation zone.

24. A process according to claim 23, wherein the overhead stream from the second distillation zone contains about 25 mol % ethyl acetate, about 68 mol % ethanol, about 6 mol % water, and about 1 mol % of other components.

25. A process according to claim 23, wherein the overhead stream from the second distillation zone is returned to the first distillation zone at a point above the feed point of the liquefiable products of the selectively hydrogenated reaction product mixture.

26. A process according to claim 18, wherein in step (f) the ethanol rich stream recovered from the bottom of the first distillation zone is subjected to treatment for the removal of water therefrom thereby to produce a relatively dry ethanol stream suitable for recycle to step (a).

27. A process according to claim 1, wherein the relatively dry ethanol stream of step (f) is recycled to step (a).

28. A process according to claim 1, wherein step (e) comprises extractive distillation with an extractive agent comprising polyethylene glycol and dipropylene glycol, diethylene glycol, or triethylene glycol.

29. A process according to claim 1, wherein step (e) comprises extractive distillation in the presence of an extractive agent containing dimethyl sulphoxide.

* * * * *